United States Patent [19]

Simon

[11] Patent Number: 5,266,381
[45] Date of Patent: Nov. 30, 1993

[54] DRY-TRANSFERS IN THE SHAPE OF EYES FOR TOUCHING UP PHOTOGRAPHS

[76] Inventor: William Simon, 46 S. 6th Ave., La Grange, Ill. 60525

[21] Appl. No.: 716,654

[22] Filed: Jun. 14, 1991

[51] Int. Cl.⁵ .............................................. B44C 1/17
[52] U.S. Cl. ..................................... 428/195; 428/15; 428/16; 428/79; 446/392
[58] Field of Search ................. 446/389, 392; 156/61, 156/63; 434/271; 428/15, 16, 195, 79, 914

[56] References Cited

U.S. PATENT DOCUMENTS

| | | | |
|---|---|---|---|
| 1,358,470 | 11/1920 | Schoenhut | 446/392 |
| 1,470,066 | 10/1923 | Dumars | 428/187 |
| 3,013,917 | 12/1961 | Karlan et al. | 428/203 X |
| 3,896,565 | 7/1975 | Quinn, III | 434/155 |
| 3,924,728 | 12/1975 | Brown et al. | 428/261 X |
| 3,942,621 | 3/1976 | Karlan | 428/914 X |
| 4,028,165 | 6/1977 | Rosenfeld | 428/204 X |
| 4,294,634 | 10/1981 | Mookil | 428/16 X |
| 4,367,252 | 1/1983 | Tordjman | 428/41 |
| 4,421,816 | 12/1983 | Arnold | 428/204 X |
| 4,639,235 | 1/1987 | Ibe | 428/16 X |

*Primary Examiner*—Henry F. Epstein
*Attorney, Agent, or Firm*—John L. Schmitt

[57] ABSTRACT

A method of touching up tainted photographs in which one or more of the posers are photographed with closed eyes, in order to form opened eyes thereon. The method utilizes dry-transfers, with each dry-transfer being formed in the shape of an eye, with the dry-transfers being provided on a backing substrate, which substrate includes a plurality of rows of eye-shaped dry-transfers, each eye-shaped dry-transfer of each row being identical, with each row of such eye-shaped dry-transfers having eye-shaped dry-transfers that are of larger size than the adjacent, lower row, in order to provide a plurality of differently-sized eye-transfers, whereby photographs taken at different distances, different lenses, and the like, may be touched up by choosing that eye-transfer that has the most suitable size for a particular photograph and person photographed.

6 Claims, 1 Drawing Sheet

DRY-TRANSFERS IN THE SHAPE OF EYES FOR TOUCHING UP PHOTOGRAPHS

BACKGROUND OF THE INVENTION

The present invention is directed to a method of touching up a photograph. Professional photographers presently must touch up a photograph when one or more of the persons in the photograph are photographed with eyes fully or partially closed, as would occur if one were photographed while blinking. The conventional method currently employed by professional photographers to touch up such "tainted" photographs is to hand-paint the eyes in over the closed eyelids, using the appropriate colors and shades thereof for forming an opened eye for the subject photographed with closed eyelids. The present invention is also directed to forming opened eyes on a "tainted" photograph where one or more persons was photographed with closed eyes. The present invention accomplishes the touching up of the photograph by means of dry-transfers formed in the shapes of eyes, whereby the dry-transfers are transferred to the photograph at the pertinent locations thereof by simply rubbing the transfers on.

The dry-transfer technology has been used for many years for transferring decals and other figures, termed indicia, from a backing sheet or substrate to a desired surface that is to receive the decal or figure. Examples of such indicia that have been transferred are letters of the alphabet. U.S. Pat. No. 3,013,917—Karlan, et al and U.S. Pat. No. 3,945,141—Frost, show such dry-transfer method and technology.

SUMMARY OF THE INVENTION

It is the primary objective of the present invention to provide a novel method of touching up tainted photographs in which one or more of the subjects are photographed with closed eyes, in order to form opened eyes in the photograph.

It is another objective of the present invention to provide such a novel method by means of dry-transfers, with each dry-transfer being formed in the shape of an eye.

It is objective of the present invention to provide the dry-transfers on a backing substrate, which substrate includes a plurality of rows of eye-shaped dry-transfers, each eye-shaped dry-transfer of each row being identical, with each row of such eye-shaped dry-transfers having eye-shaped dry-transfers that are of larger size than the adjacent, lower row, in order to provide a plurality of differently-sized eye-transfers, whereby photographs taken at different distances, with different lenses, and the like, may be touched up by choosing that eye-transfer that has the most suitable size for a particular photograph and person photographed.

It is another objective of the present invention to provide such substrates having the plurality of rows of eye-transfers in different eye-colors, such as brown, blue, gray and green, in order to touch up black-and-white as well as color photographs, and to match the color of the eyes of the subject whose was photographed with his or her eyes closed.

BRIEF DESCRIPTION OF THE DRAWINGS

The invention will be more readily understood with reference to the accompanying drawing, wherein:

FIG. 5 is a side view, in cross-section, showing how the dry-transfer is applied to the photograph; and .

DETAILED DESCRIPTION OF THE INVENTION

Figure 5:
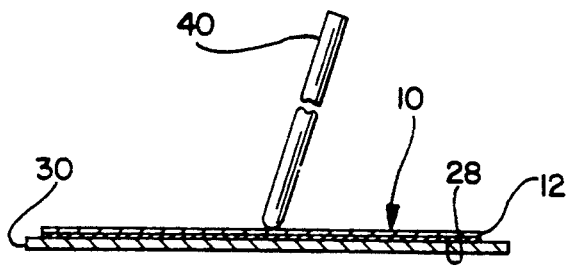
Figure 6:
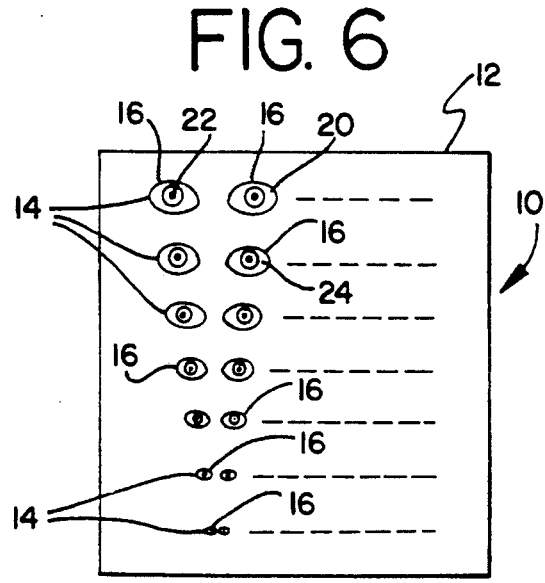
FIG. 6 is a plan view of the dry-transfer sheet with eye-shaped indicia of the invention, where a plurality of rows of eye-shaped indicia are provided on the sheet.

Referring now to the drawings in greater detail, there is shown a dry-transfer sheet 10 according to the invention as best seen in FIGS. 5 and 6. The sheet 10 comprises a backing substrate 12 made of high-impact polystyrene, preferably having a thickness of 5 mil. and a mat finish. Such a substrate 12 may be purchased from Plastic Corp. of Columbus, Ohio. In forming the sheet 10, the substrate 12 is screen-printed with a plurality of rows 14 of eye-shaped indicia 16. Each row 14 has a plurality of identical eye-transfers or indicia 16, with each row 14 of indicia 16 having a larger sized eye-indicia 16 than those of the adjacent, lower row 14, as seen in FIG. 5. The ink used is conventional screen-ink, such as that sold be Naz-Dar Corporation of Chicago, Ill. In the preferred embodiment, seven rows 14 of indicia 16 are screen-printed on the substrate 12, ranging in size from 7 mm.-length eye-shaped indicia 16, to 1 mm. in length. Each eye-shaped, dry-transfer indicia 16 is made up of three differently- colored sections: a white section 20 forming the white of the eye, a black section 22 forming the pupil of the eye, and one other section 24 of another color forming the iris of the eye. In the preferred embodiment, the color of the iris is either gray, blue, green or brown. Also, preferably, each sheet 10 is provided with the same color eye-indicia 16 for the iris, so that one sheet will be provided with blue eyes, where the iris of each eye-indicia 16 is blue, with another sheet 10 being provided with green eyes, where the iris of each eye-indicia 16 is green. Other sheets 10 will be provided with gray eyes, where the iris of the eye-indicia 16 is gray, and sheets 10 of brown eyes, where the iris of each eye-indicia 16 is brown. The sheet 10, in addition to the substrate 12 and screen-inked, eye-shaped, dry-transfer indicia 16, has an overlay 28 of conventional, clear, pressure-sensitive, dry-transfer adhesive, such as that obtainable from Pressure Graphics, Inc., of Addison, Ill. Conventional decal-lacquer may also be used as the clear adhesive overlay 28. The overlay 28 of dry-transfer adhesive is performed after the substrate 12 has been screen-printed with the indicia 16. Preferably, the entire front surface-face of the substrate 12 is coated with the dry-transfer adhesive overlay 28.

Figure 1:
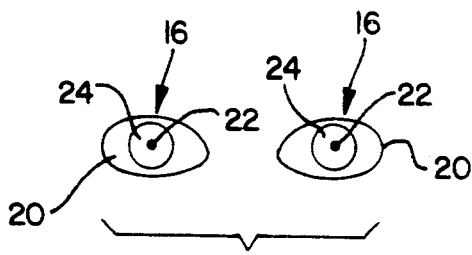
FIG. 1 is a plan view showing the shape of the dry-transfer indicia formed on a dry-transfer substrate sheet according to the invention.
Figure 2:
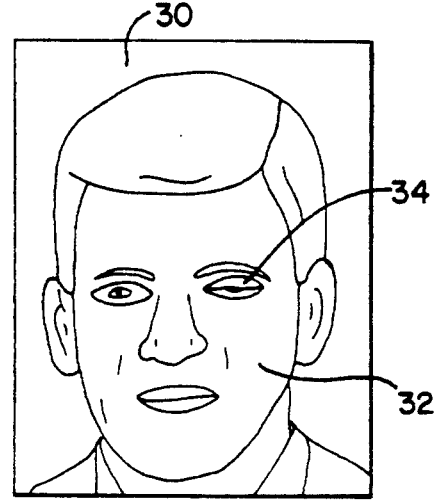
FIG. 2 is a plan view showing a photograph of a subject whose was photographed with his eyelids closed.
Figure 3:
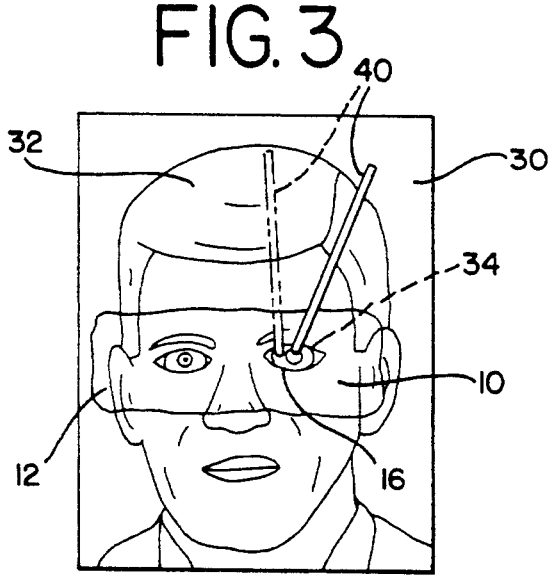
FIG. 3 is a plan view of the photograph of FIG. 2 with the dry-transfer sheet of the invention placed thereover for transferring an eye-shaped dry-transfer to the photograph to cover over a closed eyelid.
Figure 4:
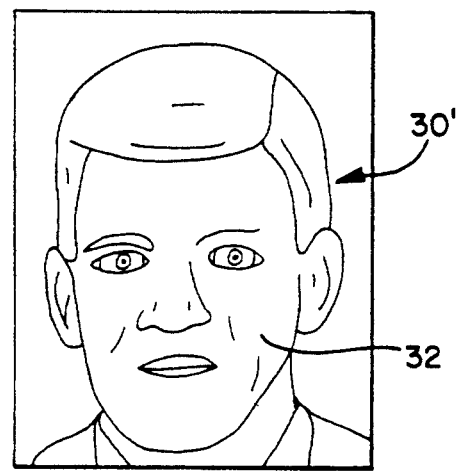
FIG. 4 is a plan view of the photograph of FIG. 2 after it has been touched up by the method of the invention, so that the subject appears with fully-opened eyes.

When using the sheet 10, as depicted in FIGS. 2-5, one first determines what size of eye-shaped, dry-transfer indicia 16 is required for touching up a the photograph 30. The particular size chosen will, of course, depend upon the size of the eye of the subject 32 whose eyelid 34 is closed, and also depends directly upon the distance from which the subject 32 was photographed, the size of the subject 32, the lens used to photograph the subject or subjects 32, and other related factors. Once the particular size of indicia 16 has been chosen, the sheet 10, which is translucent, is placed over the photograph 30, such as that shown in FIG. 2, such that one of the chosen eye-indicia 16 is placed directly on top of the closed eyelid 34 of the subject 32 whose eyes were closed or partially closed during photographic shooting. After placement of the sheet 10, it is rotated or otherwise oriented to ensure that the eye-shaped dry-transfer indicia 16 chosen will align correctly over the closed eyelid 34, and be properly oriented with respect to the remainder of the face of the subject 32 being "touched up", as seen in FIG. 3. After such proper alignment and orientation have been achieved, one then rubs the rear surface-face of the sheet 10 directly behind the chosen indicia 16 to be transferred to the photograph 30, as seen in FIG. 3. Such rubbing, with a stylus 40 or the like, in the well-known manner, causes the portion of the overlay of dry-transfer adhesive over the chosen indicia 16 to adhere to the receiving surface, which is the photograph 30, which portion of the adhesive transfers along with it the dry-transfer, eye-shaped indicia 16, since the bond of the ink of the dry-transfer image 16 to the surface of the sheet 10 is only a weak, mechanical bond, as compared to its stronger, chemical bond with the adhesive coating 28. A touched-up photograph 30' seen in FIG. 4 is thus created, where both eyes are now shown as being open.

The sheet 10 of the invention may also be used for touching up eyes of subjects 32, in photographs 30 whose eyes are completely open but whose eye color, due to lighting conditions, appear red or yellow, as is known to occur if proper lighting conditions are not present. The sheet 10 would be used in exactly the same way as described above for partially and completely closed eyelids 34, with the eye-shaped indicia 16 being transferred onto and over the eyes of the subject 32.

While a specific embodiment of the invention has been shown and described, it is to be understood that numerous changes and modifications may be made therein without departing from the scope, spirit and intent of the invention as set forth in the appended claims.

What I claim is:

1. In a dry-transfer sheet comprising dry-transfer indicia, a translucent substrate sheet upon which the indicia are mounted, and an outer coating of dry-transfer adhesive for transferring the indicia to a front side of a photograph, the improvement comprising:

said indicia comprising a plurality of different size, spaced apart, opaque, eye-representation dry-transfers for transfer to said photograph, wherein to touch up an eye of a subject depicted in said photograph said sheet is placed face down on said photograph, said sheet is moved to selectively align individual dry-transfers with the subject's eye requiring touch-up, the eye covered by the dry-transfer is compared to the subject's uncovered eye, and then the dry-transfer providing the best eye match is selectively transferred to the photograph.

2. The dry-transfer sheet according to claim 1 further characterized by, said indicia comprising a plurality of rows of said eye-representation dry-transfers, each said row having a plurality of identical, eye-representation dry-transfer indicia thereon, and the size of each said eye-representation dry-transfer of each said row being different from the size of the eye-representation dry-transfers of any other row.

3. The dry-transfer sheet according to claim 2, wherein said plurality of rows on said substrate sheet are arranged in a descending order, such that the size of said eye-representation dry-transfers in any said row is smaller than those of any other row thereabove.

4. The dry-transfer sheet according to claim 3, wherein said sheet comprises seven said rows of eye-representation dry-transfers, the size of each said eye-representation dry-transfer in the uppermost said row being 7 mm. in length, and the size of each said eye-representation dry-transfer of the lowermost said row being 1 mm. in length, and the size of each said eye-representation dry-transfer for the intermediate rows from the uppermost said row to the lowermost said row decreasing in 1 mm. increments.

5. The dry-transfer sheet according to claim 1 further characterized by, said eye-representation dry-transfers having three differently-colored sections: first white section representing the white of the eye, a second black section representing the pupil of the eye, and a third section representing the iris of the eye.

6. The dry-transfer sheet according to claim 5, wherein said third section of all of said eye-representation dry-transfers on said substrate are the same color.

* * * * *